United States Patent [19]

Ohsumi et al.

[11] 4,212,879
[45] Jul. 15, 1980

[54] BENZYL PYRROLYL METHYL CARBOXYLATE INSECTICIDES AND ACARICIDES

[75] Inventors: Tadashi Ohsumi, Kyoto; Nobushige Itaya, Nishinomiya; Masachika Hirano, Ibaraki, all of Japan

[73] Assignee: Sumitomo Chemical Company, Limited, Osaka, Japan

[21] Appl. No.: 948,049

[22] Filed: Oct. 3, 1978

[30] Foreign Application Priority Data

Oct. 7, 1977 [JP] Japan .................. 52-121244

[51] Int. Cl.² ............... A01N 9/22; C07D 207/32
[52] U.S. Cl. ................ 424/274; 260/326.34; 260/326.43; 542/429
[58] Field of Search .......... 260/326.43, 326.34; 424/274; 542/429

[56] References Cited

U.S. PATENT DOCUMENTS

| | | | |
|---|---|---|---|
| 3,268,558 | 8/1966 | Karmas | 260/326.5 R |
| 3,377,356 | 4/1968 | Ueda et al. | 260/326.43 |
| 3,847,944 | 11/1974 | Ohno et al. | 424/274 |
| 3,850,977 | 11/1974 | Itaya et al. | 424/274 |
| 3,867,542 | 2/1975 | Ueda et al. | 424/274 |
| 3,954,814 | 5/1976 | Mizutani et al. | 424/274 |
| 3,998,868 | 12/1976 | Mizutani et al. | 424/274 |
| 4,053,625 | 10/1977 | Ono et al. | 260/326.43 |

*Primary Examiner*—Donald G. Daus
*Assistant Examiner*—M. C. Eakin
*Attorney, Agent, or Firm*—Stevens, Davis, Miller & Mosher

[57] ABSTRACT

Carboxylic acid esters of the formula (I),

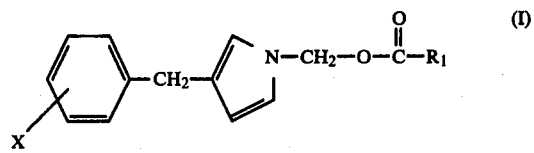

wherein X is a hydrogen atom, or a $C_1$-$C_3$ alkyl or a $C_1$-$C_3$ alkoxyl group or a halogen atom linked to the meta or para position and $R_1$ is a group of the formula (II) or (III),

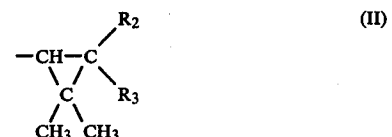

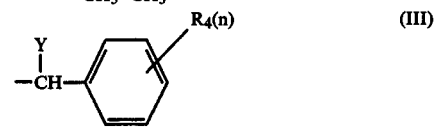

wherein $R_2$ is a hydrogen atom or a methyl group, and when $R_2$ is a methyl group $R_3$ is also a methyl group, and when $R_2$ is a hydrogen atom $R_3$ is a group of the formula,

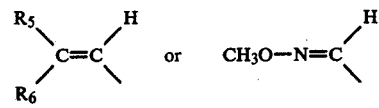

(wherein $R_5$ is a halogen atom or a $C_1$-$C_3$ alkyl, vinyl or a $C_1$-$C_3$ alkoxymethyl group, $R_6$ is a hydrogen or halogen atom or a methyl group, or, taken together, $R_5$ and $R_6$ may form a tetramethylene group by connecting together at ends thereof), $R_4$ is a halogen atom or a $C_1$-$C_3$ alkyl, $C_1$-$C_3$ alkoxyl or 3,4-methylenedioxy group, n is 1 or 2 and Y is a isopropyl or cyclopropyl group. These carboxylic acid esters are useful as insecticides and acaricides.

7 Claims, No Drawings

BENZYL PYRROLYL METHYL CARBOXYLATE INSECTICIDES AND ACARICIDES

The present invention relates to novel carboxylic acid esters of the formula (I),

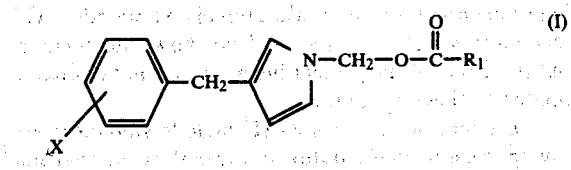

wherein X is a hydrogen atom, or a $C_1$–$C_3$ alkyl or a $C_1$–$C_3$ alkoxyl group or a halogen atom linked to the meta or para position and $R_1$ is a group of the formula (II) or (III),

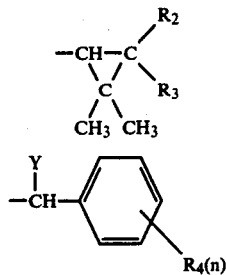

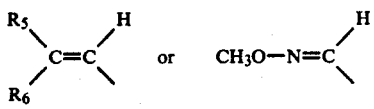

wherein $R_2$ is a hydrogen atom or a methyl group, and when $R_2$ is a methyl group $R_3$ is also a methyl group, and when $R_2$ is a hydrogen atom $R_3$ is a group of the formula, $$\underset{R_6}{\overset{R_5}{\diagdown}}C=C\underset{\diagdown}{\overset{H}{\diagup}} \quad \text{or} \quad CH_3O-N=C\underset{\diagdown}{\overset{H}{\diagup}}$$

(wherein $R_5$ is a halogen atom or a $C_1$–$C_3$ alkyl, vinyl, or a $C_1$–$C_3$ alkoxymethyl group, $R_6$ is a hydrogen or halogen atom or a methyl group, or, taken together, $R_5$ and $R_6$ may form a tetramethylene group by connecting together at ends thereof), $R_4$ is a halogen atom or a $C_1$–$C_3$ alkyl, $C_1$–$C_3$ alkoxyl or 3,4-methylenedioxy group, n is 1 or 2 and Y is a isopropyl or cyclopropyl group, a process for producing the same and insecticides and acaricides containing the same as an active ingredient.

Hitherto, there are known various insecticides of the cyclopropanecarboxylic acid ester type, and some of them are present in pyrethrum extracts. Of many insecticides now in use, these pyrethrum extracts have been widely used for controlling harmful insanitary insects and insects harmful to agricultural crops and household horticultural plants since they are very superior as insecticides in the following points: They have a very high insecticidal activity, low toxicity to mammals and rapid effect on harmful insects; and besides they make it difficult for harmful insects to acquire resistance to the pesticide. But, they are expensive so that the scope of their application is limited economically. Consequently, many homologues have been synthesized by many researchers.

From the standpoint that the foregoing drawbacks can be overcome by finding the esters having a higher insecticidal activity, the inventors particularly studied the alcohol moiety of the esters. As a result, the inventors found alcohol moieties having a higher practical value than in the conventional cyclopropanecarboxylic acid esters considering well-balanced insecticidal activity and economy. An object of the present invention is to provide insecticides comprising esters which are produced from the alcohol moieties.

For the purpose of studying the relationship between the chemical structure and biological activity of carboxylic acid ester type insecticides, the inventors tried to synthesize the below-mentioned alcohols of the formula (IV) and investigated the insecticidal activity of esters resulting from various carboxylic acids and said alcohols. As a result, the inventors found that the carboxylic acid esters of the formula (I) have superior insecticidal and acaricidal activities. Further it was confirmed that these carboxylic acid esters can be used as harmful insect-controlling agents not only for prevention of epidemics but also for agriculture, horticulture and stored cereals because they have an extremely high lethal effect and a rapid effect, and besides because they are low in toxicity to warm-blooded animals. The inventors thus attained the present invention.

Next, an explanation will be given as to synthesis of these carboxylic acid esters.

The carboxylic acid esters of the present invention can easily be obtained by reacting an alcohol of the formula (IV),

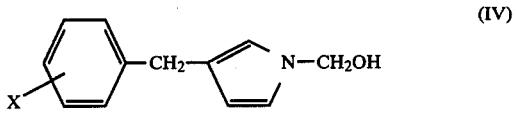

wherein X is as defined above, with an acid halide of the formula (V),

wherein $R_1$ is as defined above and Z is a halogen atom, at $-20°$ to $100°$ C. for $\frac{1}{2}$ to 10 hours in an inert solvent in the presence of an acid-binding agent. The acid halide is preferably an acid chloride. The inert solvent includes tetrahydrofuran, acetone, dioxane and the like, and the acid-binding agent includes organic tertiary amines such as triethylamine, pyridine and the like.

The carboxylic acid esters obtained by the above method can be purified, if necessary, by means such as column chromatography.

The alcohols used as material can easily be obtained by reacting a substituted 3-benzylpyrrole represented by the formula (VI),

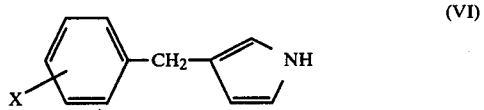

(wherein X is a hydrogen atom, or $C_1$–$C_3$ allyl or $C_1$–$C_3$ alkoxyl group, or a halogen atom linked to the meta or para position) which was synthesized in accordance with the 3-benzylpyrrole synthesis method by J. K. Groves et al., Can. J. Chem., Vol. 49, 2427 (1971), with paraformaldehyde in the presence of anhydrous potassium carbonate.

Next, an explanation will be given as to a standard method for producing the carboxylic acid esters of the formula (I).

0.05 Mole of an alcohol of the formula (IV) is dissolved in dry tetrahydrofuran, and 0.10 mole of triethylamine is added thereto. Thereafter, a solution of 0.05 mole of a carboxylic acid chloride (represented by the formula (V) wherein Z is a chlorine atom) in dry tetrahydrofuran is added dropwise thereto at 0° to 5° C. After the addition is finished, the reaction solution is stirred at the same temperature for some time, and then the reaction is further continued at room temperature. Water and ether are added to the resulting reaction solution, and the solution is separated into aqueous and organic layers. The organic layer is washed with water saturated with sodium chloride and dried over anhydrous sodium sulfate. The residue obtained after removal of the solvent is purified by chromatography on silica gel to obtain the objective ester.

The carboxylic acid esters of the formula (I) according to the present invention are novel compounds. Typical examples of the esters will be shown hereinafter, but the esters of the present invention are not of course limited to these examples.

The esters of the formula (I) include stereoisomers owing to steric configuration of the carboxylic acid and optical isomers owing to the asymmetric carbon atom of the acid. These isomeric esters are all included in the scope of the present invention.

| Compound No. | Chemical structure and name | Refractive index | | Elementary analysis | | |
|---|---|---|---|---|---|---|
| (1) | 3-(p-Chlorobenzyl)-1-pyrrolylmethyl 2,2-dimethyl-3-(2-methyl-1-propenyl)cyclopropanecarboxylate | $n_D^{26.0}$ 1.5350 | Found<br>Calculated | C: 70.81%,<br>C: 71.05%, | H: 7.23%,<br>H: 7.05%, | N: 3.92%,  Cl: 9.40%<br>N: 3.77%,  Cl: 9.53% |
| (2) | 3-(p-Bromobenzyl)-1-pyrrolylmethyl 2,2-dimethyl-3-(2-methyl-1-propenyl)cyclopropanecarboxylate | $n_D^{23.5}$ 1.5463 | Found<br>Calculated | C: 63.22%,<br>C: 63.47%, | H: 6.50%,<br>H: 6.29%, | N: 3.58%,  Br: 18.97%<br>N: 3.36%,  Br: 19.19% |
| (3) | 3-(p-Methylbenzyl)-1-pyrrolylmethyl 2,2-dimethyl-3-(2-methyl-1-propenyl)cyclopropanecarboxylate | $n_D^{24.0}$ 1.5271 | Found<br>Calculated | C: 78.34%,<br>C: 78.60%, | H: 8.60%,<br>H: 8.32%, | N: 4.15%<br>N: 3.98% |
| (4) | 3-(m-Methylbenzyl)-1-pyrrolylmethyl 2,2-dimethyl-3-(2-methyl-1-propenyl)cyclopropanecarboxylate | $n_D^{21.0}$ 1.5286 | Found<br>Calculated | C: 78.40%,<br>C: 78.60%, | H: 8.57%,<br>H: 8.32%, | N: 4.09%<br>N: 3.98% |
| (5) | 3-(p-Fluorobenzyl)-1-pyrrolylmethyl 2,2-dimethyl-3-(2,2-dichlorovinyl)cyclopropanecarboxylate | $n_D^{22.0}$ 1.5406 | Found<br>Calculated | C: 60.37%,<br>C: 60.62%, | H: 5.23%,<br>H: 5.09%, | N: 3.66%<br>N: 3.53% |

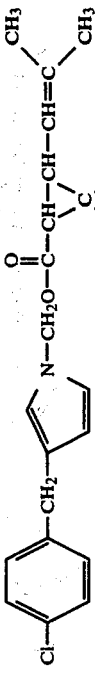
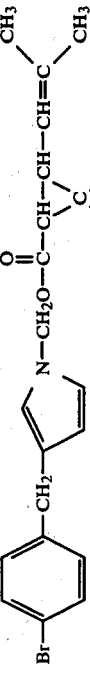
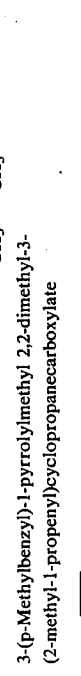
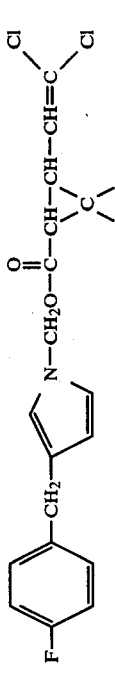

-continued

| Compound No. | Chemical structure and name | Refractive index | | Elementary analysis |
|---|---|---|---|---|
| (6) | 3-(p-Chlorobenzyl)-1-pyrrolylmethyl 2,2-dimethyl-3-(2,2-dichlorovinyl)cyclopropanecarboxylate | $n_D^{28.0}$ 1.5572 | Found<br>Calculated | C: 58.02%, H: 5.04%, N: 3.52%, Cl: 25.51%<br>C: 58.20%, H: 4.88%, N: 3.39%, Cl: 25.77% |
| (7) | 3-(m-Chlorobenzyl)-1-pyrrolylmethyl 2,2-dimethyl-3-(2,2-dichlorovinyl)cyclopropanecarboxylate | $n_D^{26.5}$ 1.5579 | Found<br>Calculated | C: 57.96%, H: 5.09%, N: 3.60%, Cl: 25.48%<br>C: 58.20%, H: 4.88%, N: 3.39%, Cl: 25.77% |
| (8) | 3-(p-Bromobenzyl)-1-pyrrolylmethyl 2,2-dimethyl-3-(2,2-dichlorovinyl)cyclopropanecarboxylate | $n_D^{26.5}$ 1.5605 | Found<br>Calculated | C: 52.38%, H: 4.65%, N: 3.20%<br>C: 52.54%, H: 4.41%, N: 3.06% |
| (9) | 3-(p-Methylbenzyl)-1-pyrrolylmethyl 2,2-dimethyl-3-(2,2-dichlorovinyl)cyclopropanecarboxylate | $n_D^{17.5}$ 1.5535 | Found<br>Calculated | C: 64.04%, H: 6.09%, N: 3.73%, Cl: 17.81%<br>C: 64.29%, H: 5.91%, N: 3.57%, Cl: 18.07% |
| (10) | 3-(p-Methoxybenzyl)-1-pyrrolylmethyl 2,2-dimethyl-3-(2,2-dichlorovinyl)cyclopropanecarboxylate | $n_D^{20.0}$ 1.5538 | Found<br>Calculated | C: 61.57%, H: 5.91%, N: 3.66%, Cl: 17.13%<br>C: 61.77%, H: 5.68%, N: 3.43%, Cl: 17.37% |

-continued

| Compound No. | Chemical structure and name | Refractive index | | Elementary analysis | | | |
|---|---|---|---|---|---|---|---|
| (11) | 3-(p-Chlorobenzyl)-1-pyrrolylmethyl 2,2-dimethyl-3-(2,2-dibromovinyl)cyclopropanecarboxylate | $n_D^{24.0}$ 1.5763 | Found Calculated | C: 47.63%, C: 47.89%, | H: 4.25%, H: 4.02%, | N: 2.91% N: 2.79% | |
| (12) | 3-(p-Bromobenzyl)-1-pyrrolylmethyl 2,2-dimethyl-3-(2,2-dibromovinyl)cyclopropanecarboxylate | $n_D^{24.5}$ 1.5782 | Found Calculated | C: 43.70%, C: 43.99%, | H: 3.88%, H: 3.69%, | N: 2.69%, N: 2.56%, | Br: 43.72% Br: 43.90% |
| (13) | 3-(m-Bromobenzyl)-1-pyrrolylmethyl 2,2-dimethyl-3-(2,2-dibromovinyl)cyclopropanecarboxylate | $n_D^{24.0}$ 1.5788 | Found Calculated | C: 43.72%, C: 43.99%, | H: 3.81%, H: 3.69%, | N: 2.72%, N: 2.56%, | Br: 43.69% Br: 43.90% |
| (14) | 3-(p-Methoxybenzyl)-1-pyrrolylmethyl 2,2-dimethyl-3-(2,2-dibromovinyl)cyclopropanecarboxylate | $n_D^{22.5}$ 1.5701 | Found Calculated | C: 50.44%, C: 50.69%, | H: 4.83%, H: 4.66%, | N: 2.98%, N: 2.82%, | Br: 32.03% Br: 32.14% |
| (15) | 3-(p-Chlorobenzyl)-1-pyrrolylmethyl 2,2,3,3-tetramethylcyclopropanecarboxylate | $n_D^{26.0}$ 1.5115 | Found Calculated | C: 69.21%, C: 69.45%, | H: 7.23%, H: 6.99%, | N: 4.23%, N: 4.05%, | Cl: 10.02% Cl: 10.25% |

-continued

| Compound No. | Chemical structure and name | Refractive index | | Elementary analysis |
|---|---|---|---|---|
| (16) | 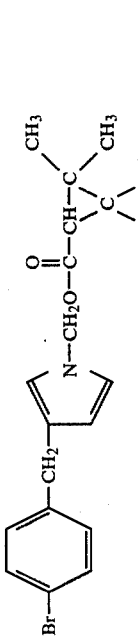<br>3-(p-Bromobenzyl)-1-pyrrolylmethyl 2,2,3,3-tetramethylcyclopropanecarboxylate | $n_D^{25.0}$ 1.5156 | Found<br>Calculated | C: 61.33%, H: 6.48%, N: 3.70%, Br: 20.22%<br>C: 61.54%, H: 6.20%, N: 3.59%, Br: 20.47% |
| (17) | 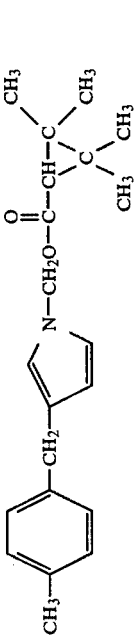<br>3-(p-Methylbenzyl)-1-pyrrolylmethyl 2,2,3,3-tetramethylcyclopropanecarboxylate | $n_D^{23.5}$ 1.5080 | Found<br>Calculated | C: 77.23%, H: 8.54%, N: 4.54%<br>C: 77.50%, H: 8.36%, N: 4.30% |
| (18) | 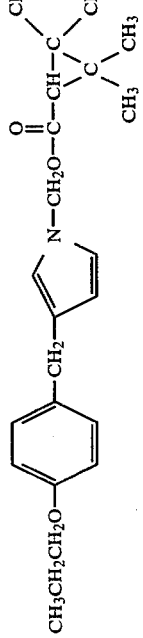<br>3-(p-Propyloxybenzyl)-1-pyrrolylmethyl 2,2,3,3-tetramethylcyclopropanecarboxylate | $n_D^{22.5}$ 1.5124 | Found<br>Calculated | C: 74.49%, H: 8.69%, N: 3.92%<br>C: 74.76%, H: 8.46%, N: 3.79% |
| (19) | 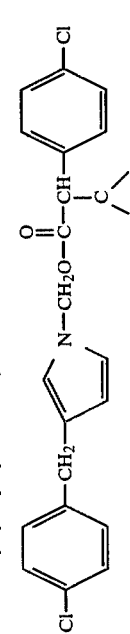<br>3-(p-Chlorobenzyl)-1-pyrrolylmethyl cyclopropyl-(p-chlorophenyl)acetate | $n_D^{22.0}$ 1.5563 | Found<br>Calculated | C: 66.54%, H: 5.23%, N: 3.49%, Cl: 16.98%<br>C: 66.67%, H: 5.11%, N: 3.38%, Cl: 17.11% |
| (20) | 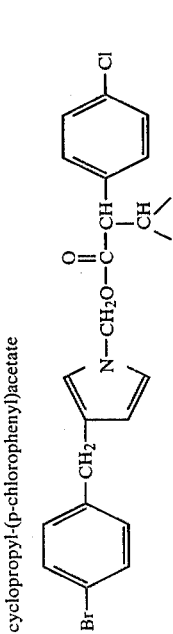<br>3-(p-Bromobenzyl)-1-pyrrolylmethyl cyclopropyl-(p-chlorophenyl)acetate | $n_D^{22.0}$ 1.5593 | Found<br>Calculated | C: 60.00%, H: 4.87, N: 3.28%<br>C: 60.21%, H: 4.61%, N: 3.05% |

-continued

| Compound No. | Chemical structure and name | Refractive index | | Elementary analysis | | | |
|---|---|---|---|---|---|---|---|
| (21) | 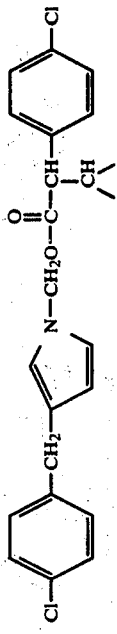<br>3-(p-Chlorobenzyl)-1-pyrrolylmethyl 2-(p-chlorophenyl)isovalerate | $n_D^{25.0}$ 1.5558 | Found<br>Calculated | C: 66.12%,<br>C: 66.35%, | H: 5.85%,<br>H: 5.57%, | N: 3.64%,<br>N: 3.36%, | Cl: 16.85%<br>Cl: 17.03% |
| (22) | 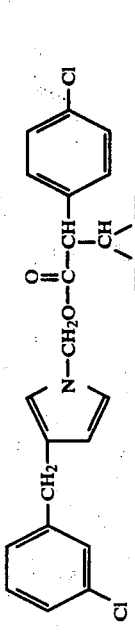<br>3-(m-Chlorobenzyl)-1-pyrrolylmethyl 2-(p-chlorophenyl)isovalerate | $n_D^{25.0}$ 1.5581 | Found<br>Calculated | C: 66.17%,<br>C: 66.35%, | H: 5.79%,<br>H: 5.57%, | N: 3.58%,<br>N: 3.36%, | Cl: 16.91%<br>Cl: 17.03% |
| (23) | 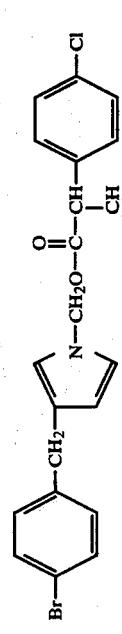<br>3-(p-Bromobenzyl)-1-pyrrolylmethyl 2-(p-chlorophenyl)isovalerate | $n_D^{25.0}$ 1.5693 | Found<br>Calculated | C: 59.72%,<br>C: 59.95%, | H: 5.23%,<br>H: 5.03%, | N: 3.27%<br>N: 3.04% | |
| (24) | 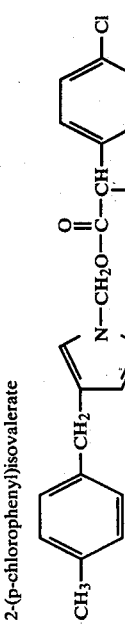<br>3-(p-Methylbenzyl)-1-pyrrolylmethyl 2-(p-chlorophenyl)isovalerate | $n_D^{17.5}$ 1.5561 | Found<br>Calculated | C: 72.55%,<br>C: 72.81%, | H: 6.90%,<br>H: 6.62%, | N: 3.71%,<br>N: 3.54%, | Cl: 8.69%<br>Cl: 8.95% |
| (25) | 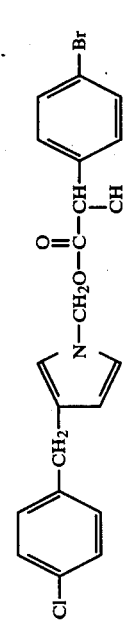<br>3-(p-Chlorobenzyl)-1-pyrrolylmethyl 2-(p-bromophenyl)isovalerate | $n_D^{23.0}$ 1.5600 | Found<br>Calculated | C: 59.80%,<br>C: 59.95%, | H: 5.17%,<br>H: 5.03%, | N: 3.30%<br>N: 3.04% | |

-continued

| Compound No. | Chemical structure and name | Refractive index | | Elementary analysis | | | |
|---|---|---|---|---|---|---|---|
| (26) | 3-(p-Bromobenzyl)-1-pyrrolylmethyl 2-(p-bromophenyl)isovalerate | $n_D^{23.0}$ 1.5652 | Found<br>Calculated | C: 54.41%,<br>C: 54.68%, | H: 4.82%,<br>H: 4.59%, | N: 3.03%,<br>N: 2.77%, | Br: 31.40%<br>Br: 31.63% |
| (27) | 3-(p-Methoxybenzyl)-1-pyrrolylmethyl 2-(p-bromophenyl)isovalerate | $n_D^{24.0}$ 1.5597 | Found<br>Calculated | C: 62.88%,<br>C: 63.16%, | H: 5.98%,<br>H: 5.74%, | N: 3.31%,<br>N: 3.07%, | Br: 17.23%<br>Br: 17.51% |
| (28) | 3-(p-Chlorobenzyl)-1-pyrrolylmethyl 2-(p-methoxyphenyl)isovalerate | $n_D^{26.5}$ 1.5551 | Found<br>Calculated | C: 69.73%,<br>C: 69.98%, | H: 6.51%,<br>H: 6.36%, | N: 3.62%,<br>N: 3.40%, | Cl: 8.42%<br>Cl: 8.61% |
| (29) | 3-(p-Bromobenzyl)-1-pyrrolylmethyl 2-(p-methoxyphenyl)isovalerate | $n_D^{25.0}$ 1.5605 | Found<br>Calculated | C: 62.92%,<br>C: 63.16%, | H: 5.98%,<br>H: 5.74%, | N: 3.29%,<br>N: 3.07%, | Br: 17.22%<br>Br: 17.51% |
| (30) | 3-(p-Chlorobenzyl)-1-pyrrolylmethyl 2-(p-methylphenyl)isovalerate | $n_D^{20.5}$ 1.5564 | Found<br>Calculated | C: 72.63%,<br>C: 72.81%, | H: 6.81%,<br>H: 6.62%, | N: 3.66%,<br>N: 3.54%, | Cl: 8.70%<br>Cl: 8.95% |

-continued

| Compound No. | Chemical structure and name | Refractive index | | Elementary analysis | | | |
|---|---|---|---|---|---|---|---|
| (31) | 3-(p-Bromobenzyl)-1-pyrrolylmethyl 2-(p-methylphenyl)isovalerate | $n_D^{25.0}$ 1.5609 | Found Calculated | C: 65.20%, C: 65.46%, | H: 5.22%, H: 5.95%, | N: 3.30%, N: 3.18%, | Br: 18.00% Br: 18.14% |
| (32) | 3-(p-Propylbenzyl)-1-pyrrolylmethyl 2-(p-methylphenyl)isovalerate | $n_D^{26.0}$ 1.5419 | Found Calculated | C: 80.09%, C: 80.36%, | H: 8.49%, H: 8.24%, | N: 3.63% N: 3.47% | |
| (33) | 3-(p-Chlorobenzyl)-1-pyrrolylmethyl 2-(3,4-methylenedioxyphenyl)isovalerate | $n_D^{26.0}$ 1.5554 | Found Calculated | C: 67.44%, C: 67.68%, | H: 5.90%, H: 5.68%, | N: 3.42%, N: 3.29%, | Cl: 8.06% Cl: 8.32% |
| (34) | 3-(p-Bromobenzyl)-1-pyrrolylmethyl 2-(3,4-methylenedioxyphenyl)isovalerate | $n_D^{26.0}$ 1.5583 | Found Calculated | C: 61.14%, C: 61.29%, | H: 5.33%, H: 5.14%, | N: 3.20%, N: 2.98%, | Br: 16.73% Br: 16.99% |
| (35) | 3-Benzyl-1-pyrrolylmethyl 2,2-dimethyl-3-(2,2-dichlorovinyl)cyclopropanecarboxylate | $n_D^{24.0}$ 1.5533 | Found Calculated | C: 63.32%, C: 63.50%, | H: 5.79%, H: 5.60%, | N: 3.88%, N: 3.70%, | Cl: 18.60% Cl: 18.74% |

-continued

| Compound No. | Chemical structure and name | Refractive index | | Elementary analysis | | |
|---|---|---|---|---|---|---|
| (36) | 3-Benzyl-1-pyrrolylmethyl 2,2-dimethyl-3-(2,2-difluorovinyl)cyclopropanecarboxylate | $n_D^{24.0}$ 1.5106 | Found<br>Calculated | C: 69.30%,<br>C: 69.55%, | H: 6.40%,<br>H: 6.13%, | N: 4.29%<br>N: 4.06% |
| (37) | 3-Benzyl-1-pyrrolylmethyl 2,2-dimethyl-3-(2,2-dibromovinyl)cyclopropanecarboxylate | $n_D^{30.0}$ 1.5742 | Found<br>Calculated | C: 51.21%,<br>C: 51.42%, | H: 4.68%,<br>H: 4.53%, | N: 3.13%, Br: 34.15%<br>N: 3.00%, Br: 34.21% |
| (38) | 3-Benzyl-1-pyrrolylmethyl 2,2-dimethyl-3-(2-methyl-1-propenyl)cyclopropanecarboxylate | $n_D^{32.0}$ 1.5300 | Found<br>Calculated | C: 78.04%,<br>C: 78.30%, | H: 8.27%,<br>H: 8.06%, | N: 4.38%<br>N: 4.15% |
| (39) | 3-Benzyl-1-pyrrolylmethyl 2,2,3,3-tetramethyl-cyclopropanecarboxylate | $n_D^{30.0}$ 1.5077 | Found<br>Calculated | C: 76.75%,<br>C: 76.89%, | H: 8.62%,<br>H: 8.39%, | N: 4.55%<br>N: 4.48% |
| (40) | 3-Benzyl-1-pyrrolylmethyl 2,2-dimethyl-3-(2-methylbutadienyl)cyclopropanecarboxylate | $n_D^{29.0}$ 1.5413 | Found<br>Calculated | C: 78.79%,<br>C: 79.05%, | H: 7.98%,<br>H: 7.98%, | N: 4.22%<br>N: 4.01% |

-continued

| Compound No. | Chemical structure and name | Refractive index | | Elementary analysis | | |
|---|---|---|---|---|---|---|
| (41) | 3-Benzyl-1-pyrrolylmethyl 2,2-dimethyl-3-(cyclopentylidenemethyl)cyclopropanecarboxylate | $n_D^{27.0}$ 1.5328 | Found<br>Calculated | C: 79.01%,<br>C: 79.30%, | H: 8.26%,<br>H: 8.04%, | N: 4.03%<br>N: 3.85% |
| (42) | 3-Benzyl-1-pyrrolylmethyl 2,2-dimethyl-3-(methoxyiminomethyl)cyclopropanecarboxylate | $n_D^{31.0}$ 1.5294 | Found<br>Calculated | C: 70.32%,<br>C: 70.57%, | H: 7.33%,<br>H: 7.11%, | N: 8.50%<br>N: 8.23% |
| (43) | 3-Benzyl-1-pyrrolylmethyl 2-(p-chlorophenyl)isovalerate | $n_D^{30.0}$ 1.5513 | Found<br>Calculated | C: 72.09%,<br>C: 72.34%, | H: 6.58%,<br>H: 6.33%, | N: 3.90%, Cl: 9.03%<br>N: 3.67%, Cl: 9.28% |
| (44) | 3-Benzyl-1-pyrrolylmethyl 2-(m-chlorophenyl)isovalerate | $n_D^{30.0}$ 1.5522 | Found<br>Calculated | C: 72.11%,<br>C: 72.34%, | H: 6.57%,<br>H: 6.33%, | N: 3.86, Cl: 9.10%<br>N: 3.67%, Cl: 9.28% |
| (45) | 3-Benzyl-1-pyrrolylmethyl 2-(p-methylphenyl)isovalerate | $n_D^{30.0}$ 1.5431 | Found<br>Calculated | C: 79.50%,<br>C: 79.74%, | H: 7.81%,<br>H: 7.53%, | N: 3.99%<br>N: 3.87% |

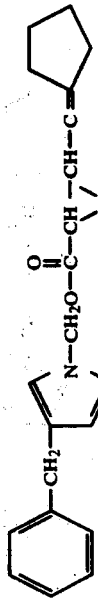
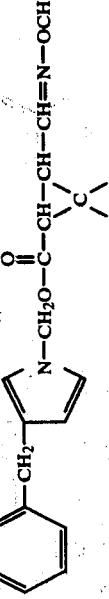
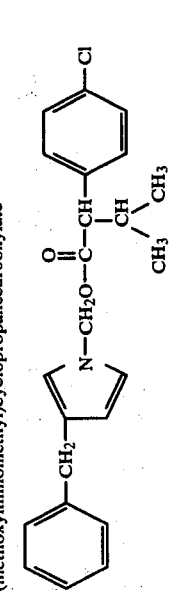
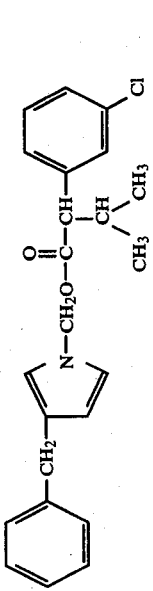
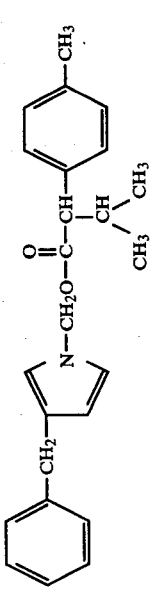

| Compound No. | Chemical structure and name | Refractive index | | Elementary analysis | | |
|---|---|---|---|---|---|---|
| (46) | 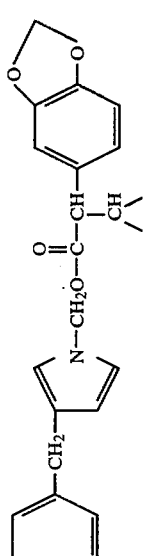<br>3-Benzyl-1-pyrrolylmethyl 2-(3,4-methylenedioxyphenyl)isovalerate | $n_D^{31.0}$ 1.5508 | Found<br>Calculated | C: 73.42%,<br>C: 73.64%, | H: 6.65%,<br>H: 6.44%, | N: 3.76%<br>N: 3.58% |
| (47) | 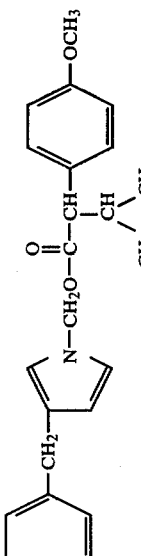<br>3-Benzyl-1-pyrrolylmethyl 2-(p-methoxyphenyl)isovalerate | $n_D^{29.0}$ 1.5510 | Found<br>Calculated | C: 76.14%,<br>C: 76.36%, | H: 7.43%,<br>H: 7.21%, | N: 3.87%<br>N: 3.71% |
| (48) | 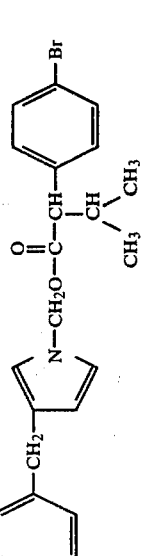<br>3-Benzyl-1-pyrrolylmethyl 2-(p-bromophenyl)isovalerate | $n_D^{30.0}$ 1.5603 | Found<br>Calculated | C: 64.73%,<br>C: 64.79%, | H: 5.72%,<br>H: 5.67%, | N: 3.41%, Br: 18.59%<br>N: 3.29%, Br: 18.04% |
| (49) | 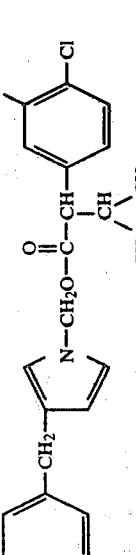<br>3-Benzyl-1-pyrrolylmethyl 2-(3,4-dichlorophenyl)isovalerate | $n_D^{32.0}$ 1.5983 | Found<br>Calculated | C: 66.10%,<br>C: 66.35%, | H: 5.79%,<br>H: 5.57%, | N: 3.58%, Cl: 16.75%<br>N: 3.36%, Cl: 17.03% |
| (50) | 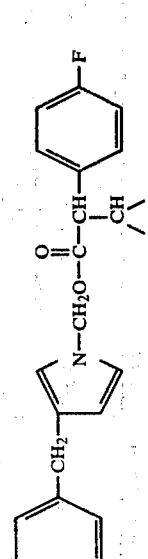<br>3-Benzyl-1-pyrrolylmethyl 2-(p-fluorophenyl)isovalerate | $n_D^{29.0}$ 1.5387 | Found<br>Calculated | C: 75.31%,<br>C: 75.59%, | H: 6.90%,<br>H: 6.62%, | N: 4.05%, F: 5.01%<br>N: 3.83%, F: 5.20% |

Next, examples of synthesis of typical compounds among the foregoing carboxylic acid esters will be illustrated with reference to the following examples.

EXAMPLE 1

2.01 g (10.0 mmole) of 3-(p-methylbenzyl)-1-pyrrolylmethanol and 2.02 g (20.0 mmole) of triethylamine are dissolved in 30 ml of dry tetrahydrofuran. Thereafter, 2.28 g (10.0 mmole) of 2,2-dimethyl-3-(2,2-dichlorovinyl)cyclopropanecarbonyl chloride is dissolved in 5 ml of dry tetrahydrofuran, and this solution is added dropwise to the above solution which is kept at 5° C. or less with stirring and ice-cooling. After the addition is finished, stirring is continued for a further 5 hours at room temperature.

Ether is added to the resulting reaction solution, and the solution is washed with water saturated with sodium chloride. The organic layer is dried over anhydrous sodium sulfate and concentrated.

The residue is purified chromatographically with a column packed with silica gel to obtain 3.59 g of 3-(p-methylbenzyl)-1-pyrrolylmethyl 2,2-dimethyl-3-(2,2-dichlorovinyl)cyclopropanecarboxylate as a pale yellow liquid (yield 91%; $n_D^{17.5}1.5535$).

EXAMPLE 2

2.00 g (7.5 mmole) of 3-(p-bromobenzyl)-1-pyrrolylmethanol and 1.50 g (15 mmole) of triethylamine are dissolved in 30 ml of dry tetrahydofuran. Thereafter, 1.73 g (7.5 mmole) of 2-(p-chlorophenyl)isovalerate is dissolved in 5 ml of dry tetrahydrofuran, and this solution is added dropwise to the above solution which is kept at 5° C. or less with stirring and ice-cooling.

After the addition is finished, stirring is continued for a further 5 hours at room temperature.

Ether is added to the resulting reaction solution, and the solution is washed with water saturated with sodium chloride. The organic layer is dried over anhydrous sodium sulfate and concentrated.

The residue is purified chromatographically with a column packed with silica gel to obtain 3.07 g of 3-(p-bromobenzyl)-1-pyrrolylmethyl 2-(p-chlorophenyl)-isovalerate as a pale yellow liquid (yield 89%; $n_D^{26.0}1.5693$).

EXAMPLE 3

Synthesis of 3-benzylpyrrole 12.0 g (52.4 mmole) of methyl 4-benzoyl-2-pyrrolecarboxylate, 8.79 g (157 mmole) of potassium hydroxide and 10.5 g (210 mmole) of hydrazine hydrate are dissolved in 150 ml of triethylene glycol. Reaction is carried out by stirring the solution at 120° C. for 2 hours and then at 160° C. for 3 hours in an atmosphere of nitrogen gas. After reaction is finished, the reaction solution is allowed to cool and poured into ice water, followed by extraction with ether. The extract is washed with water saturated with sodium chloride and concentrated. The residue is distilled under reduced pressure to obtain 5.86 g of 3-benzylpyrrole as a colorless liquid. Yield 71.2%. $n_D^{29.5}$ 1.5790. Boiling point 95°–98° C. (0.09 mmHg).

EXAMPLE 4

Synthesis of 3-benzyl-1-pyrrolylmethanol 2.18 g (13.9 mmole) of 3-benzylpyrrole, 0.42 g (13.9 mmole) of paraformaldehyde and 0.07 g (0.5 mmole) of anhydrous potassium carbonate are mixed and stirred at 50° C. for 4 hours in an atmosphere of nitrogen. Dry tetrahydrofuran is added to the reaction solution and filtered. The filtrate is concentrated to obtain 2.53 g of 3-benzyl-1-pyrrolylmethanol as a pale yellow liquid. Yield 97.3%. $n_D^{31.5}1.5837$.

The present compounds of the formula (I) are very effective for controlling harmful insanitary insects such as flies, mosquitoes and cockroaches, insects harmful to agricultural crops such as planthoppers, leafhoppers, army worms and cut worms, diamond-back moth, tortorixes, aphids and mites, insects harmful to stored cereals such as grain mite, indian meal moth and rice weevils, animal-parasitic lice and mites, and other harmful insects. Further, the compounds of the present invention not only knock down the harmful insects to death, but also they have repellency so that they display an effect of keeping harmful insects away from their host plants. The compounds of the present invention can be practically used in various preparation forms.

In order to demonstrate the excellent effects of the present compounds more clearly, experimental examples on the typical compounds will be shown. Other compounds of the formula (I) have a similar tendency.

EXPERIMENTAL EXAMPLE 1

A 10% emulsifiable concentrate of each of the present compounds (1) to (50) was prepared by mixing 10 parts of the present compound, 15 parts of Sorpol SM-200 (a registered trade mark of Tōhō Kagaku Co., mixture of nonionic surfactant and anionic surfactant) and 75 parts of xylene.

The bottom of a polyethylene cup (diameter 5.5 cm) was covered with filter paper of the same size. Each of the emulsifiable concentrates was diluted 200 times with water (corresponding to 500 ppm), and 0.7 ml of the dilute solution was dropped down to the filter paper. Thereafter, 30 mg of sucrose was placed on the paper as bait. Ten house-fly female adults (Musca domestica) were liberated therein, and the cup was covered. The dead and alive were examined after 48 hours and mortality was obtained (2 repetitions).

| Test compound | Mortality (%) |
| --- | --- |
| (1) | 100 |
| (2) | 100 |
| (3) | 100 |
| (4) | 100 |
| (5) | 100 |
| (6) | 100 |
| (7) | 100 |
| (8) | 100 |
| (9) | 100 |
| (10) | 100 |
| (11) | 100 |
| (12) | 100 |
| (13) | 100 |
| (14) | 100 |
| (15) | 100 |
| (16) | 100 |
| (17) | 100 |
| (18) | 100 |
| (19) | 100 |
| (20) | 100 |
| (21) | 100 |
| (22) | 100 |
| (23) | 100 |
| (24) | 100 |
| (25) | 100 |
| (26) | 100 |
| (27) | 100 |
| (28) | 100 |
| (29) | 100 |
| (30) | 100 |

-continued

| Test compound | Mortality (%) |
|---|---|
| (31) | 100 |
| (32) | 100 |
| (33) | 100 |
| (34) | 100 |
| (35) | 100 |
| (36) | 100 |
| (37) | 100 |
| (38) | 100 |
| (39) | 100 |
| (40) | 100 |
| (41) | 100 |
| (42) | 100 |
| (43) | 100 |
| (44) | 100 |
| (45) | 100 |
| (46) | 100 |
| (47) | 100 |
| (48) | 100 |
| (49) | 100 |
| (50) | 100 |

EXPERIMENTAL EXAMPLE 2

Each of the present compounds and control compounds was dissolved in acetone to prepare an acetone solution of a pre-determined concentration. Thereafter, 0.5 μl of the solution was applied, by means of a microsyringe, to the ventral thorax of house-fly female adults (*Musca domestica*) each anaesthetized with carbon dioxide gas. The treated adults were liberated in a plastic cup (diameter 10 cm, height 4 cm) in which a bait (3% sugar water) was placed. After 24 hours, the dead and alive were examined to obtain mortality, and the value of $LD_{50}$ was obtained from the mortality according to the Finney's graphic method.

| Test compound | $LD_{50}$ (μg/fly) |
|---|---|
| (1) | 0.061 |
| (5) | 0.050 |
| (6) | 0.024 |
| d-Trans acid isomer of (6) | 0.011 |
| (9) | 0.028 |
| (15) | 0.020 |
| (21) | 0.054 |
| S(+)-acid isomer of (21) | 0.027 |
| (33) | 0.060 |
| Allethrin | 0.52 |
| Phenothrin* | 0.34 |
| Pyrethrins | 0.74 |

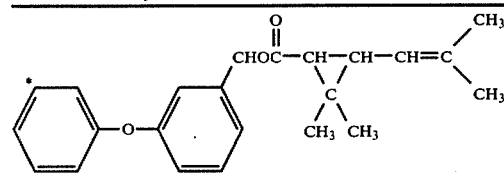

EXPERIMENTAL EXAMPLE 3

The present compounds formulated in the same manner as in Experimental Example 1 and 10% emulsifiable concentrates of the control compounds were diluted with water to a pre-determined concentration. Thereafter, 200 ml of the dilute solution was placed in a 300-ml glass beaker, and 30 full grown larvae of Northern house mosquito (*Culex pipiens pallens*) were liberated therein. After 24 hours, the dead and alive were examined to obtain mortality. The value of $LC_{50}$ was then obtained from the mortality according to the Finney's graphic method.

| Test compound | $LC_{50}$ (ppm) |
|---|---|
| (35) | 0.0056 |
| d-Cis acid isomer of (37) | 0.0021 |
| (39) | 0.0076 |
| (41) | 0.0065 |
| (43) | 0.015 |
| S(+)-acid isomer of (43) | 0.0082 |
| (50) | 0.018 |
| Allethrin | 0.13 |
| Resmethrin* | 0.021 |
| Phenothrin** | 0.060 |

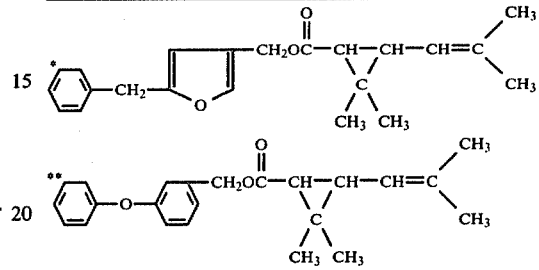

EXPERIMENTAL EXAMPLE 4

The present compounds formulated in the same manner as in Experimental Example 1 and 10% emulsifiable concentrates of the control compounds were diluted with water to a pre-determined concentration. Third instar larvae of tobacco cut worm (*Spodoptera litura*) and cabbage leaves were dipped for 30 seconds in the dilute solution, air-dried and placed in a plastic up (diameter 11 cm). After 48 hours, the dead and alive were examined.

| Test compound | Concentration (ppm) and mortality (%) | |
|---|---|---|
| | 100 ppm | 25 ppm |
| (2) | 100 (%) | 80 (%) |
| (6) | 100 | 100 |
| (7) | 100 | 90 |
| (9) | 100 | 100 |
| (11) | 100 | 100 |
| (17) | 100 | 85 |
| (24) | 100 | 100 |
| (35) | 100 | 100 |
| (36) | 100 | 100 |
| (38) | 100 | 90 |
| (39) | 100 | 100 |
| (43) | 100 | 100 |
| (47) | 100 | 90 |
| (49) | 100 | 90 |
| Allethrin | 60 | 0 |
| Phenothrin | 95 | 45 |
| DDVP | 40 | 0 |

In formulating the present compounds of the formula (I) into insecticides or acaricides, the compounds can be changed, like the conventional pyrethroid type compounds, into optional preparation forms using carriers for the common insecticides, by the methods well known to the skilled in the art. That is, the compounds can be formulated into oil sprays, emulsifiable concentrates, dusts, aerosols, wettable powders, granules, mosquito coils, other heating or non-heating fumigants, powdery or solid baits containing attractants, or other preparation forms.

Further, a more superior insecticidal activity can be developed by combining two or more of the present compounds, and besides the insecticidal effect of the present compounds can be increased by combining the compounds and synergists for pyrethroid such as α-[2-(2-butoxyethoxy)ethoxy]-4,5-methylenedioxy-2-propyltoluene (referred to as piperonylbutoxide hereinafter), 1,2-methylenedioxy-4-[2-(octylsulfinyl)propyl]benzene (referred to as sulfoxide hereinafter), 4-(3,4-methylenedioxyphenyl)-5-methyl-1,3-dioxane (referred to as sufroxane hereinafter), N-(2-ethylhexyl)-bicyclo[2,2,1]-hepta-5-ene-2,3-dicarboximide (referred to as MGK-264 hereinafter), octachlorodipropy ether (referred to as S-421 hereinafter) and isobornylthiocyanoacetate (referred to as Thanite hereinafter), or well-known effective synergists for allethrin or pyrethrins.

In general, the carboxylic acid esters tend to be inferior in resistance to light, heat and oxidation. Accordingly, compositions having a more stable effect can be prepared by adding a proper amount of stabilizing agents, if necessary. The stabilizing agents include antioxidants and ultraviolet absorbers such as phenol derivatives (e.g. BHT, BHA), bisphenol derivatives, arylamine derivatives (e.g. phenyl-α-naphthylamine, phenyl-β-naphthylamine, condensation products of phenetidine and acetone) and benzophenone compounds.

Additionally, the present compounds can be formulated into multipurpose compositions having a superior activity by combining the compounds and other active ingredients such as allethrin, N-(chrysanthemoxymethyl)-3,4,5,6-tetrahydrophthalimide (referred to as tetramethrin hereinafter), 5-benzyl-3-furylmethyl chrysanthemate [hereinafter referred to as Chrysron (a registered trade mark of Sumitomo Chemical Co.)], 3-phenoxybenzyl chrysanthemate, 5-propargylfurfuryl chrystanthemate, 2-methyl-5-propargyl-3-furylmethyl chrysanthemate; d-trans- or d-cis,trans-acid isomers thereof; pyrethrum extracts; d-trans- or d-cis,trans-acid isomers of d-allethrolone; 3-phenoxybenzyl 2,2-dimethyl-3-(2,2-dichlorovinyl)cyclopropanecarboxylate, α-cyano-3-phenoxybenzyl 2′,2′-dimethyl-3′-(2,2-dichlorovinyl)-cyclopropanecarboxylate, α-cyano-3-phenoxybenzyl 2,′2′,3′,3′-tetramethylcyclopropanecarboxylate, α-cyano-3-phenoxybenzyl 2-(4-chlorophenyl)isovalerate and other well-known cyclopropanecarboxylic acid esters; organo-phosphorus type insecticides such as O,O-dimethyl-O-(3-methyl4-nitrophenyl)-phosphorothioate [hereinafter referred to as Sumithion (a registered trade mark of Sumitomo Chemical Co., Ltd.)], O,O-dimethyl-O-4-cyanophenylphosphorothioate [hereinafter referred to as Cyanox (a registered trade mark of Sumitomo Chemical Co., Ltd.)], O,O-dimethyl-O-(2,2-dichlorovinyl)phosphate (hereinafter referred to as Dichlorvos), Baycid, Vinyphate, Dipterex, Diazinon, Malathion, Salithion and Papthion (the latter three are registered trade marks of Sumitomo Chemical Co., Ltd.); carbamate type insecticides such as 1-naphthyl-N-methylcarbamate, 3,4-dimthylphenyl-N-methylcarbamate, 3-methylphenyl-N-methylcarbamate, 2-isopropoxyphenyl-N-methylcarbamate and S-methyl-N-(methylcarbamoyloxy)thioacetoimidate; N′-(2-methyl-4-chlorophenyl)-N,N-dimethylformamidine; 1,3-bis(-carbamoylthio)-2-(N,N-dimethylamino)propane hydrochloride; other insecticides, acaridicides, fungicides, nematocides, plant growth regulators, microbial insecticides such as B.T. preparation (*Bacillus thuringiensis*) and B.M. preparation (*Bacillus moritai*), insect hormone compounds, herbicides, fertilizers and other agricultural chemicals. Furthermore, a synergistic effect due to combination with these active ingredients can also be expected.

Preparation of the present insecticides and acaricides will be illustrated with reference to the following preparation examples.

PREPARATION EXAMPLE 1

0.2 Part of each of the present compounds (1) to (50) is dissolved in kerosene, and the total weight is made up to 100 parts. Thus an oil spray is obtained.

PREPARATION EXAMPLE 2

0.05 Part of each of the present compounds (3) to (47) and 0.25 part of piperonylbutoxide are dissolved in kerosene, and the total weight is made up to 100 parts. Thus an oil spray is obtained.

PREPARATION EXAMPLE 3

Twenty parts of each of the present compounds (1) to (34), 10 parts of Sorpol 3005X (a registered trade mark of Tōhō Kagaku Co., mixture of nonionic surfactant and anionic surfactant) and 70 parts of xylene are mixed. The mixture is then thoroughly mixed to make a solution. Thus an emulsifiable concentrate is obtained.

PREPARATION EXAMPLE 4

Twenty parts of each of the present compounds (35) to (50), 15 parts of Sorpol SM-200 (a registered trade mark of Tōhō Kagaku Co., mixture of nonionic surfactant and anionic surfactant) and 65 parts of xylene are mixed. The mixture is then thoroughly mixed to make a solution. Thus an emulsifiable concentrate is obtained.

PREPARATION EXAMPLE 5

Ten parts of each of the present compounds (1), (6), (28), (33), (34), (36), (37), (42), (43) and (50), 20 parts of S-421, 15 parts of Sorpol SM-200 (the same as above) and 55 parts of xylene are mixed. The mixture is then thoroughly mixed to make a solution. Thus an emulsifiable concentrate is obtained.

PREPARATION EXAMPLE 6

0.1 Part of each of the present compounds (15) and (49), 0.2 part of tetramethrin, 7 parts of xylene and 7.7 parts of deodorized kerosene are well mixed to make a solution. The solution is filled in an aerosol container. After attaching a valve portion to the container, 85 parts of a propellant (liquefied petroleum gas) is charged therein under pressure through the valve. Thus an aerosol is obtained.

PREPARATION EXAMPLE 7

0.2 Part of the present compound (1), 0.1 part of the d-trans acid isomer of allethrin, 7 parts of xylene and 7.7 parts of deodorized kerosene are well mixed to obtain a solution. The solution is filled in an aerosol container. An aerosol is then obtained by the same procedure as in Preparation example 6.

PREPARATION EXAMPLE 8

0.2 Part of the present compound (35), 0.1 part of the d-trans acid isomer of allethrin, 7 parts of xylene and 7.7 parts of deodorized kerosene are well mixed to make a solution. Separately from this, 0.2 part of the present compound (42), 0.2 part of Chrysron (the same as above), 7 parts of xylene and 7.6 parts of deodorized kerosene are well mixed to make a solution. Each solution is filled in an aerosol container. The aerosol of each present compound is then obtained by the same procedure as in Preparation example 6.

PREPARATION EXAMPLE 9

0.15 Gram of each of the present compounds (1), (5), (15), (18), (28), (39), (40), (43), (46) and (48) and 0.2 g of the d-trans acid isomer of allethrin are mixed and dissolved in 20 ml of methanol. The solution is uniformly mixed with 99.65 g of a mosquito coil carrier (blending ratio of Tabu powder to Pyrethrum marc to wood powder is 3:5:1) with stirring, and then methanol is evaporated. To the residue obtained is added 150 ml of water, and the mixture is kneaded thoroughly, shaped into a mosquito coil and dried. Thus a mosquito coil is obtained.

PREPARATION EXAMPLE 10

To 0.02 g of the present compound (15) are added 0.05 g of 5-propargyl-furfuryl dl-cis,trans-chrysanthemate and 0.1 g of BHT, and the mixture is dissolved in a suitable amount of chloroform. Thereafter, a filter paper of 3.5 cm × 1.5 cm × 0.3 cm (thick) is impregnated uniformly with the resulting solution. Thus a fibrous fumigant for heating on a hot plate is obtained.

Materials having an effect equivalent to pulp plate such as filter paper, for example, asbestos may also be used as a fibrous carrier.

PREPARATION EXAMPLE 11

To 0.02 g of the present compound (44) are added 0.05 g of 5-propargyl-furfuryl dl-cis,trans-chrysanthemate and 0.1 g of BHT, and the mixture is dissolved in a suitable amount of chloroform. Thereafter, a filter paper of 3.5 cm × 1.5 cm × 0.3 cm (thick) is impregnated uniformly with the resulting solution.

Thus a fibrous fumigant for heating on a hot plate is obtained.

PREPARATION EXAMPLE 12

To 20 parts of each of the present compounds (5), (7), (9), (12), (16), (21), (39), (41), (43), (46) and (50) and the d-cis isomer of the present compound (3) are added 10 parts of Sumithion (the same as above) and 5 parts of Sorpol SM-200 (the same as above), and the mixture is thoroughly mixed. Thereafter, 65 parts of 300 mesh diatomaceous earth is further added thereto and the mixture is well mixed in a mortar with stirring. Thus a wettable powder is obtained.

PREPARATION EXAMPLE 13

To 1 part of each of the d-cis isomers of the present compounds (2), (4), (36) and (38) is added 2 parts of 3-methylphenyl-N-methylcarbamate. The mixture is dissolved in 20 parts of acetone, and 97 parts of 300 mesh talc is added thereto. After thoroughly mixing in a mortar with stirring, acetone is removed by evaporation. Thus a dust is obtained.

PREPARATION EXAMPLE 14

To 3 parts of each of the present compounds (1), (6), (8), (11), (19), (35), (36), (42), (45) and (49) are added 5 parts of Toyolignin CT (a registered trade mark of Tōyō Spinning Co.) and 92 parts of GSM Clay (a registered trade mark of Zieklite Mining Co.). The mixture is then well mixed while being stirred in a mortar.

Thereafter, the mixture is mixed with water of 10% based thereon, well mixed with stirring, granulated by means of a granulator and air-dried. Thus a granular preparation is obtained.

PREPARATION EXAMPLE 15

To 2 parts of each of the present compounds (4), (5), (6), (7), (8), (10), (12), (17), (30), (38) (39), (41), (42), (44) and (46) are added 2 parts of Cyanox (the same as above), 5 parts of Toyolignin CT (a registered trade mark of Tōyō Spinning Co., lignin sulfonate derivative) and 91 parts of GSM Clay (a registered trade mark of Zieklite Mining Co., silica powder). The mixture is then well mixed while being stirred in a mortar.

Thereafter, the mixture is mixed with water of 10% based thereon, well mixed with stirring, granulated by means of a granulator and air-dried. Thus a fine granular preparation is obtained.

PREPARATION EXAMPLE 16

0.1 Part of the d-trans acid isomer of each of the present compounds (9) and (36), 0.2 part of the d-trans acid isomer of allethrin, 11.7 parts of deodorized kerosene and 1 part of Atmos 300 (emulsifier made of glycerides of fatty acids, a registered trade mark of Atlas Chemical Co.) are mixed and emulsified with addition of 50 parts of distilled water. An aerosol container is then filled with the resulting emulsion and 37 parts of a 3:1 mixture of deodorized butane to deodorized propane. Thus a water-based aerosol is obtained.

The insecticidal and acaricidal effects of the present esters will be illustrated in more detail with reference to the following application examples.

APPLICATION EXAMPLE 1

Five milliliters of each of the oil sprays obtained in Preparation examples 1 and 2 was sprayed, according to the Campbell's turntable method [Soap and Sanitary Chemicals, Vol. 14, No. 6, 119 (1938)]. About 100 house-fly adults (*Musca domestica*) per group was exposed to the descending mist for 10 minutes. By the next day, more than 80% of the flies were killed in each case.

APPLICATION EXAMPLE 2

Ten third to fourth instar larvae of diamondback moth (*Plutella xylostella*) were liberated in a glass Petri dish of 14 cm in diameter. Three milliliters of a 200-fold aqueous dilute solution of each emulsifiable concentrate obtained according to Preparation example 5 was sprayed by means of a rotary spraying tower.

Thereafter, the larvae were liberated in a glass Petri dish in which Chinese cabbage leaves were previously placed. After two days, 100% of the larvae were killed in each case.

APPLICATION EXAMPLE 3

The insecticidal activity on house-fly adults (*Musca domestica*) of each aerosol obtained according to Preparation examples 6, 7 and 16 was tested by the aerosol test method (Soap and Chemical Specialities, Blue Book, 1965) using a (6 ft)$^3$ Peet Grady's chamber. Thus, with any aerosol, more than 80% of the flies could be knocked down 15 minutes after spraying and more than 70% of the flies could be killed by the next day.

APPLICATION EXAMPLE 4

About 50 Northern house mosquito female adults (*Culex pipiens pallens*) were liberated in a (70 cm)$^3$ glass chamber in which a battery-type small electric fan (wing diameter 13 cm) was set and driven.

0.2 Gram of each of the mosquito coils obtained in Preparation example 9 was ignited at one end and placed at the center of the bottom of the chamber. With any mosquito coil, more than 90% of the adults could be knocked down within 20 minutes.

APPLICATION EXAMPLE 5

About 50 house-fly adults (*Musca domestica*) were liberated in a (70 cm)$^3$ glass chamber in which a battery-type small electric fan (wing diameter 13 cm) was set and driven.

Each of the fumigants obtained in Preparation example 10 was placed on a hot plate in the chamber and fumigated. More than 90% of the house-flies could be knocked down within 20 minutes with any fumigant.

APPLICATION EXAMPLE 6

Each of the dusts obtained in Preparation example 13 was applied on rice seedlings in a pot (diameter 10 cm), which had elapsed 20 days after sowing, under pressure of 200 mmHg at a rate of 2 kg/10 are by means of a Bell jar duster. After application, the seedlings were covered with a wire cage, and about 20 green rice leafhopper adults (*Nephotettix cincticeps*) were liberated therein. After 24 hours, the dead and alive were examined and it was found that mortality was 100%.

APPLICATION EXAMPLE 7

Ten liters of water was placed in a 14-liter polypropylene bucket, and 1 g of each of the granular preparations obtained in Preparation example 14 was added thereto. After one day, about 50 full grown Northern house mosquito larvae (*Culex pipiens pallens*) were liberated in the water. The dead and alive were examined, and more than 90% of the larvae could be killed within 24 hours in each case.

APPLICATION EXAMPLE 8

Carmine mite female adults (*Tetranychus cinnabarinus*) were made parasitic on the leaves of potted kidney beans (primordial leaf stage) which had elapsed 9 days after sowing, at a rate of 10–15/leaf, and bred at 27° C. for a week in a constant temperature room. Then, numerous carmine mites were found to be bred at various growth stages. At this time, the 100-fold aqueous dilute solution of each of the emulsifiable concentrates, which were obtained in Preparation example 3 using the present compounds (5), (6), (8), (9), (39), (42) and (43), respectively, was sprayed at a rate of 10 ml/pot by means of a turn table. After 10 days, damage of the kidney beans by the mites was examined, but damage was hardly observed in any case.

What is claimed is:

1. A compound of the formula (I),

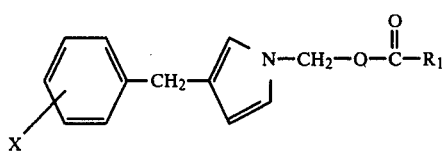

wherein X is a hydrogen atom, or a $C_1$–$C_3$ alkyl or a $C_1$–$C_3$ alkoxyl group or a halogen atom linked to the meta or para position and $R_1$ is a group of the formula (II) or (III),

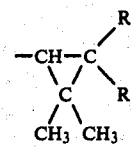
(II)

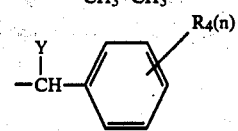
(III)

wherein $R_2$ is a hydrogen atom or a methyl group, and when $R_2$ is a methyl group $R_3$ is also a methyl group, and when $R_2$ is a hydrogen atom $R_3$ is a group of the formula,

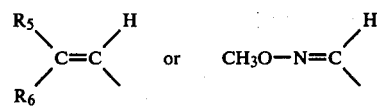

wherein $R_5$ is a halogen atom or a $C_1$–$C_3$ alkyl, vinyl or a $C_1$–$C_3$ alkoxymethyl group, $R_6$ is a hydrogen or halogen atom or a methyl group, or taken together, $R_5$ and $R_6$ may form a tetramethylene group by connecting together at ends thereof, $R_4$ is a halogen atom or a lower alkyl, lower alkoxyl or 3,4-methylenedioxy group, n is 1 or 2 and Y is a isopropyl or cyclopropyl group, the esters of the formula (I) including stereoisomers owing to steric configuration of the carboxylic acid and optical isomers owing to the asymmetric carbon of the acid.

2. The compound according to claim 1, wherein X is a hydrogen atom, or a $C_1$–$C_3$ alkyl or $C_1$–$C_3$ alkoxyl group or a halogen atom linked to the meta or para position and $R_1$ is a group of the formula (II),

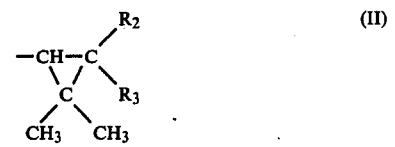
(II)

wherein $R_2$ is a hydrogen atom and $R_3$ is a group of the formula,

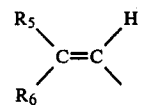

wherein $R_5$ is a halogen atom or a $C_1$–$C_3$ alkyl, $R_6$ is a hydrogen or halogen atom or methyl group, the above esters including stereoisomers owing to steric configuration of the carboxylic acid and optical isomers owing to the asymmetric carbon of the acid.

3. The compound according to claim 1, wherein X is a hydrogen atom, and $R_1$ is a 3-(2,2-dichlorovinyl)-2,2-dimethylcyclopropyl group including its stereoisomer owing to steric configuration of the carboxylic acid and its optical isomer owing to the asymmetric carbon of the acid.

4. The compound according to claim 1, wherein X is a hydrogen atom, and $R_1$ is a 2,2-dimethyl-3-(2-methyl-1-propenyl)-cyclopropyl group including its stereoisomer owing to steric configuration of the carboxylic acid and its optical isomer owing to the asymmetric carbon of the acid.

5. The compound according to claim 1, wherein X is a 4-chlorine atom and R₁ is a 3-(2,2-dichlorovinyl)-2,2-dimethylcyclopropyl group including its stereoisomer owing to steric configuration of the carboxylic acid and its optical isomer owing to the asymmetric carbon of the acid.

6. An insecticidal and acaricidal composition which comprises as an active ingredient an insecticidally and acaricidally effective amount of the compound according to claim 1 and an inert carrier.

7. A method for controlling insects and acarids which comprises applying an insecticidally and acaricidally effective amount of the compound according to claim 1 to insects and acarids.

* * * * *